United States Patent
Hotta et al.

(10) Patent No.: US 6,823,875 B2
(45) Date of Patent: Nov. 30, 2004

(54) COMPOSITION OF A VIBRATING WAVE TYPE ORAL CLEANSING AND HYGIENE APPLIANCE

(76) Inventors: Kunio Hotta, P.O. Box No. 6-57, Chung-Ho City, Taipei Hsien 235 (TW); Sei Kato, P.O. Box No. 6-57, Chung-Ho City, Taipei Hsien 235 (TW)

(*) Notice: Subject to any disclaimer, the term of this patent is extended or adjusted under 35 U.S.C. 154(b) by 0 days.

(21) Appl. No.: 10/014,870

(22) Filed: Dec. 14, 2001

(65) Prior Publication Data

US 2003/0111091 A1 Jun. 19, 2003

(51) Int. Cl.[7] ............................................. A61C 15/00
(52) U.S. Cl. ...................................................... 132/322
(58) Field of Search ................................ 132/322, 329, 132/323; 601/139, 141, 142; 15/22.1, 22.2; 433/89

(56) References Cited

U.S. PATENT DOCUMENTS

| | | | | |
|---|---|---|---|---|
| 2,467,221 A | * | 4/1949 | Pastl ............................ | 132/323 |
| 4,011,616 A | * | 3/1977 | Kennedy ...................... | 132/323 |
| 4,863,380 A | * | 9/1989 | Creed ........................... | 433/89 |
| 5,033,150 A | * | 7/1991 | Gross et al. ................... | 15/22.1 |
| 5,170,809 A | * | 12/1992 | Imai et al. .................... | 132/322 |
| 5,261,430 A | * | 11/1993 | Mochel ........................ | 132/322 |
| 5,718,667 A | * | 2/1998 | Sugimoto et al. ........... | 601/139 |
| 5,722,440 A | * | 3/1998 | Urso ............................. | 132/323 |
| 6,047,711 A | * | 4/2000 | Wagner ........................ | 132/322 |
| 6,474,347 B1 | * | 11/2002 | Hallinder et al. ............ | 132/325 |

* cited by examiner

*Primary Examiner*—Todd E. Manahan
*Assistant Examiner*—Robyn Kieu Doan
(74) *Attorney, Agent, or Firm*—Troxell Law Office PLLC

(57) ABSTRACT

A composition of a vibrating wave type oral cleansing and hygiene appliance, more especially a hygiene appliance, utilizing the manner of vibrating and agitating wave to drive a cleansing floss material to provide rapid plaque removing for the external surfaces on the gaps between the teeth and on the tooth root as well as to provide massage and hygiene for the tooth root and the gums. The appliance including a holder body with a working section and an insert section situated at the front end for assembling a link rod, the free end of the link rod is designed as a floss bow section to provide expansion of the cleansing floss material, one distal end of the insert section is disposed for assembling a massage bar with horseshoe-shaped contact press end, thereby to achieve the effect of cleansing and massaging.

5 Claims, 7 Drawing Sheets

COMPOSITION OF A VIBRATING WAVE TYPE ORAL CLEANSING AND HYGIENE APPLIANCE

BACKGROUND OF THE INVENTION

Accordingly, the general dental cleansing involves brushing the oral cavity and the teeth, since the way of teeth arrangement and the teeth are implanted on the gums, the aged phenomenon occurs after long-term chewing movement, larger cracks might be formed at the related and included gaps between the tooth root section and the flesh substance, thereby food remains tends to accumulate thereat; the gap between two adjacent teeth is hard to be reached by a regular toothbrush, therefore the situation of left plague usually happens inside the said gap; when the gums are attacked by diseases, the neutron alternation provided therefrom will slow down and the force of supporting the composition of the teeth will gradually reduce, therefore, hygiene provided for the teeth and the gums is very necessary.

SUMMARY OF THE INVENTION

Therefore, the primary objective of the present invention is to especially utilize the method of vibrating wave to enable the cleansing floss to form a pointed cylindrical vibrating axis at the gap between the teeth, to utilize the high efficient frequency of the vibrating wave to conduct rapid cleansing on the tooth surfaces between the tooth gaps, to utilize the vibrating wave to efficiently massage the teeth, and to utilize an extra massage bar to vigorously massage the gums or the teeth.

Another objective of the present invention is that through the movable fix clamping of the insert section between the link rod disposed with a floss bow section and the holder body, the expanding operation can be achieved; the expansion changes the vibration amplitude according to the width of the gap between the teeth thereby to facilitate the user's application.

Yet another objective of the present invention is to have two elastic clamp components disposed at the insert slot mounted inside the said insert section for the inserting disposal of the link rods with different thickness thereby to provide wider coupling for other cleansing tools.

Still another objective of the present invention is that the said working section can be mounted with a long shaft motor, the extending of the long shaft moves the said working section to the front end of the holder body for mounting and concentrates the vibrating energy at the front end.

The further objective of the present invention is that the floss material connected at the floss bow section of the link rod can adapt the winding manner of movable assembly.

To enable a further understanding of the present invention, the brief description of the drawings below is followed by the detailed description of the preferred embodiment.

DETAILED DESCRIPTION OF THE PREFERRED EMBODIMENTS

Figure 1:
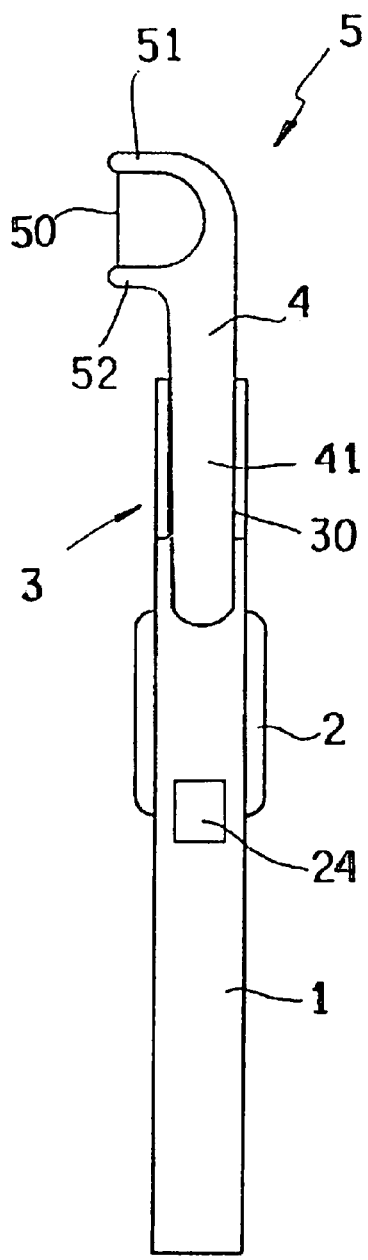
FIG. 1 is a schematic drawing of the lateral view of the assembled present invention.

Referring to FIG. 1, the present invention achieves a composition of a vibrating wave type oral cleansing and hygiene appliance, more especially a composition of a hygiene appliance providing the cleansing for the gap between teeth arranged in the oral cavity and the hygienic operation for the teeth and the gums, mainly comprises of a holder body (1) with a working section (2) disposed therein, the outward front end of the said working section (2) is mounted with an insert section (3), an insert slot (30) is disposed inside the said insert section (3), the said insert slot (30) provides the insertion of a rod body (41) mounted on a link rod (4), the free end of the said link rod (4) is disposed with a floss bow section (5), the said floss bow section (5) utilizes the expansion between two relative floss expansion ends (51, 52) to expand a cleansing floss material (50), a power switch (24) is mounted on the holder body (1).

Figure 2:
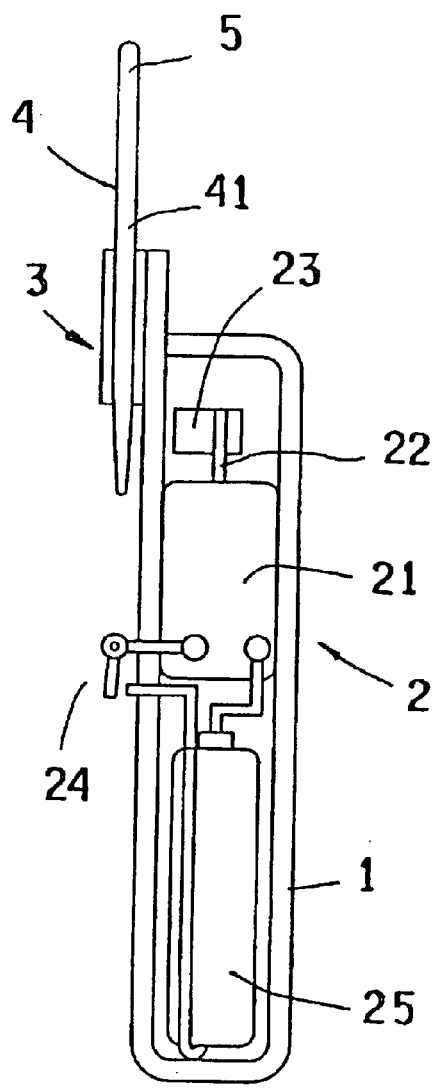
FIG. 2 is a cross-sectional drawing of bird's-eye view of the components of the present invention.

Referring to FIG. 2, the said power switch (24) is connected to the electric control between a power source (25) and a motor (21); the working section (2) disposed inside the holder body (1) utilizes the motor (21), through an axle center (22) thereof, to link an eccentric hammer (23); the insert section (3) directly couples with the rod body (41) mounted on the link rod (4) to achieve a certain vibrating wave through the eccentric function of the said working section (2) thereby to provide the operation of vibrating function for the floss bow section (5).

Figure 3:
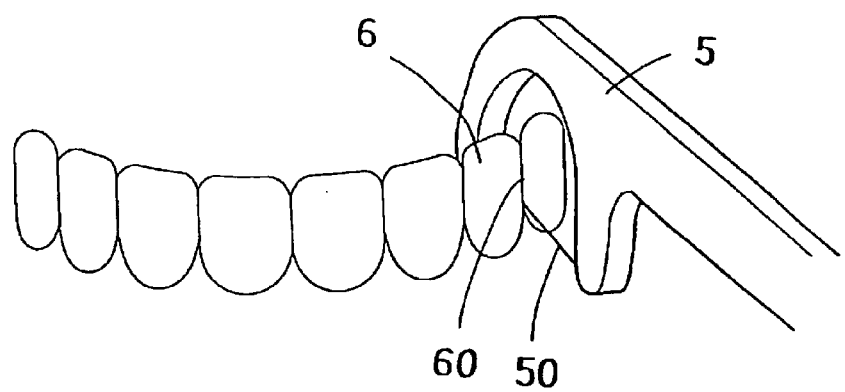
FIG. 3 is the first schematic drawing of the operation of the floss bow section of the present invention.

Referring to FIG. 3, through the user's manual holding of the holder body (1), the floss bow section (5) connected with the floss material (50) enables the floss material (50) to cut into the inner section of the tooth gap (60) between the teeth (6), the manual cleansing operation toward the tooth gap (60) can thereby be conducted as a common non-power-driven operation.

Figure 4:
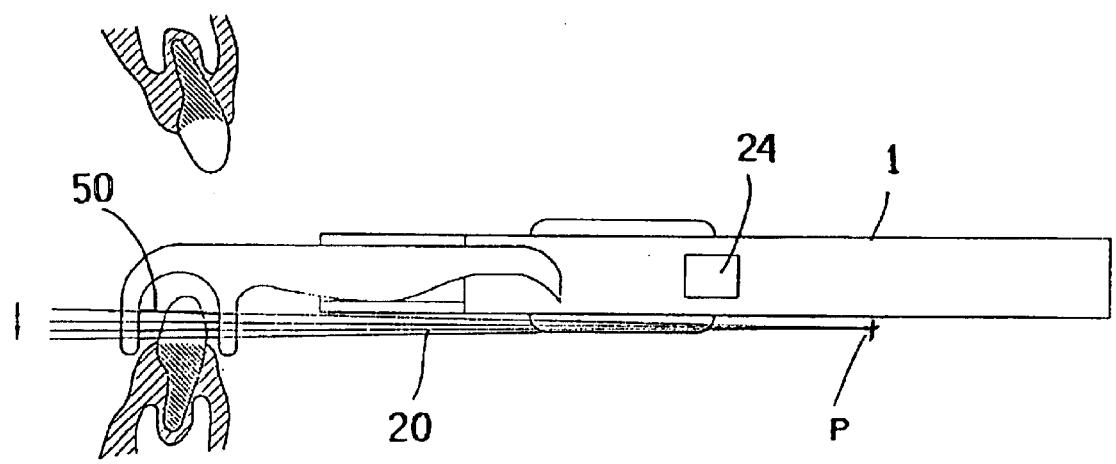
FIG. 4 is the second schematic drawing of the operation of the floss bow section of the present invention.

Referring to FIG. 4, when the switch (24) is started to work, the said floss material (50) and the entire holder body (1) will generate a vibrating wave centered by the central point of a circle (P) to enable the floss material (50) to make coning vibration following the axle turning range of the vibrating axis (20).

Figure 5:
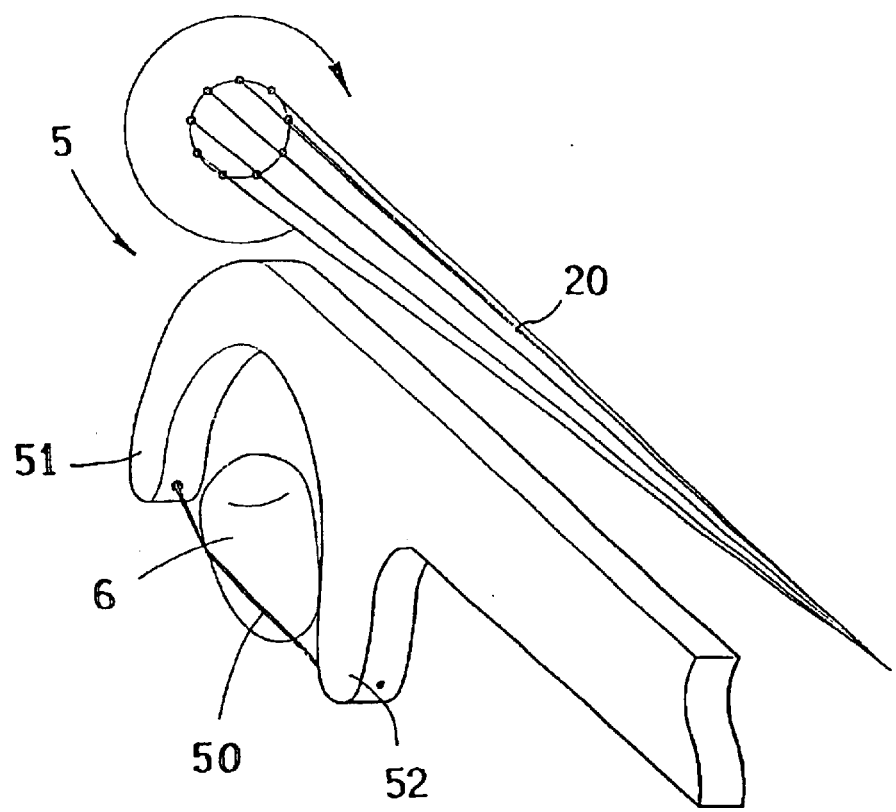
FIG. 5 is the first schematic drawing of the operation of the working manner of the floss material of the present invention.

Referring to FIG. 5, the said vibrating axis (20) is in the shape of a coning cylinder, therefore the floss material (50) tied on the floss bow section (5) can cut and press the surfaces of the teeth (6) as well as utilize the rod body of the floss material (50) to efficiently pick out the plaque attached on the surfaces of the teeth (6); the said floss material (50) is connected between the floss expansion ends (51, 52), the expansion thereof enables the floss material (50) to obtain the expansion so as to provide specific operation of the force for cut pressing and removing; when the force of cut pressing is operated manually and exerted in a bigger manner, the floss material (50) will deform when the rod body (41) is under the situation of being manually operated by the user; utilizing the bending and deforming of the said floss material (50) and the deformed arc line, the scrapping operation on the larger areas of the surfaces of the teeth (6) can be increased.

Figure 6:
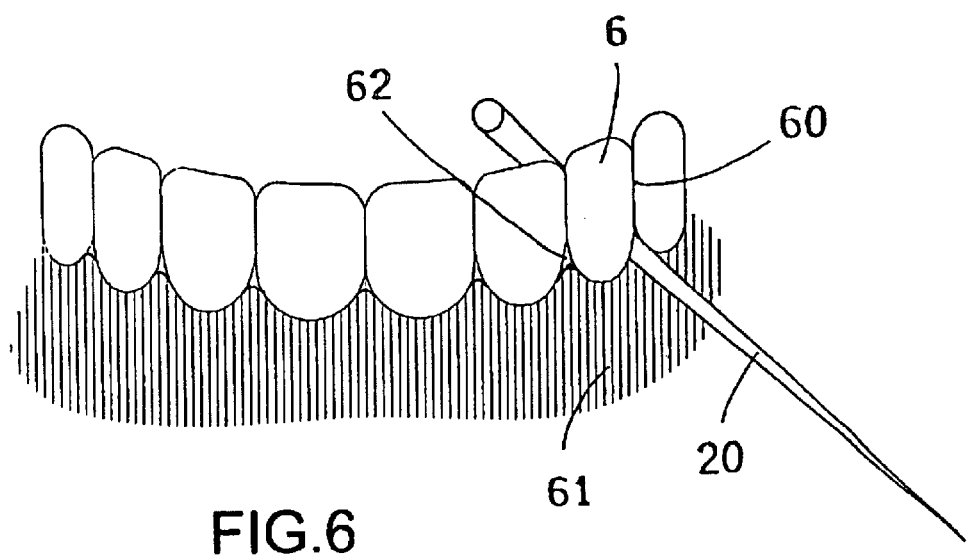
FIG. 6 is the second schematic drawing of the operation of the working manner of the floss material of the present invention.

Referring to FIG. 6, the said vibrating axis (20) can correspondingly clean a larger space of the interface between the root section of the tooth gaps (60) and the gums (61); a triangular space (62) often forms between the root section of the teeth (6) and the gums (61), the said vibrating axis (20) can be used to conduct rapid cleansing on the said triangular space (62), (of course, the amount of force exerted for the operation will cause a certain influence on the flesh surface of the gums (61); as the same, any kind of cleansing method including the brushing of the toothbrush will cause injury if the applied force toward the gums (61) is exerted too strong, therefore the force degree of the cleansing should be properly controlled by the user's feeling so as to prevent generating injury on the surfaces of the gums (61)), thereby to utilize the method of the present invention can rapidly cleanse the tooth gaps (60) and the relative space (62) of the tooth root; to utilize the said vibrating wave enables the floss material (50) not only to remove the plaque on the surfaces of the teeth (6), but also to relatively utilize the said vibrating wave to conduct entire massage for the teeth (6) and to further reach the gum (61) section thereby to achieve the dual effect of massage and tooth cleansing simultaneously.

Figures 7, 8:
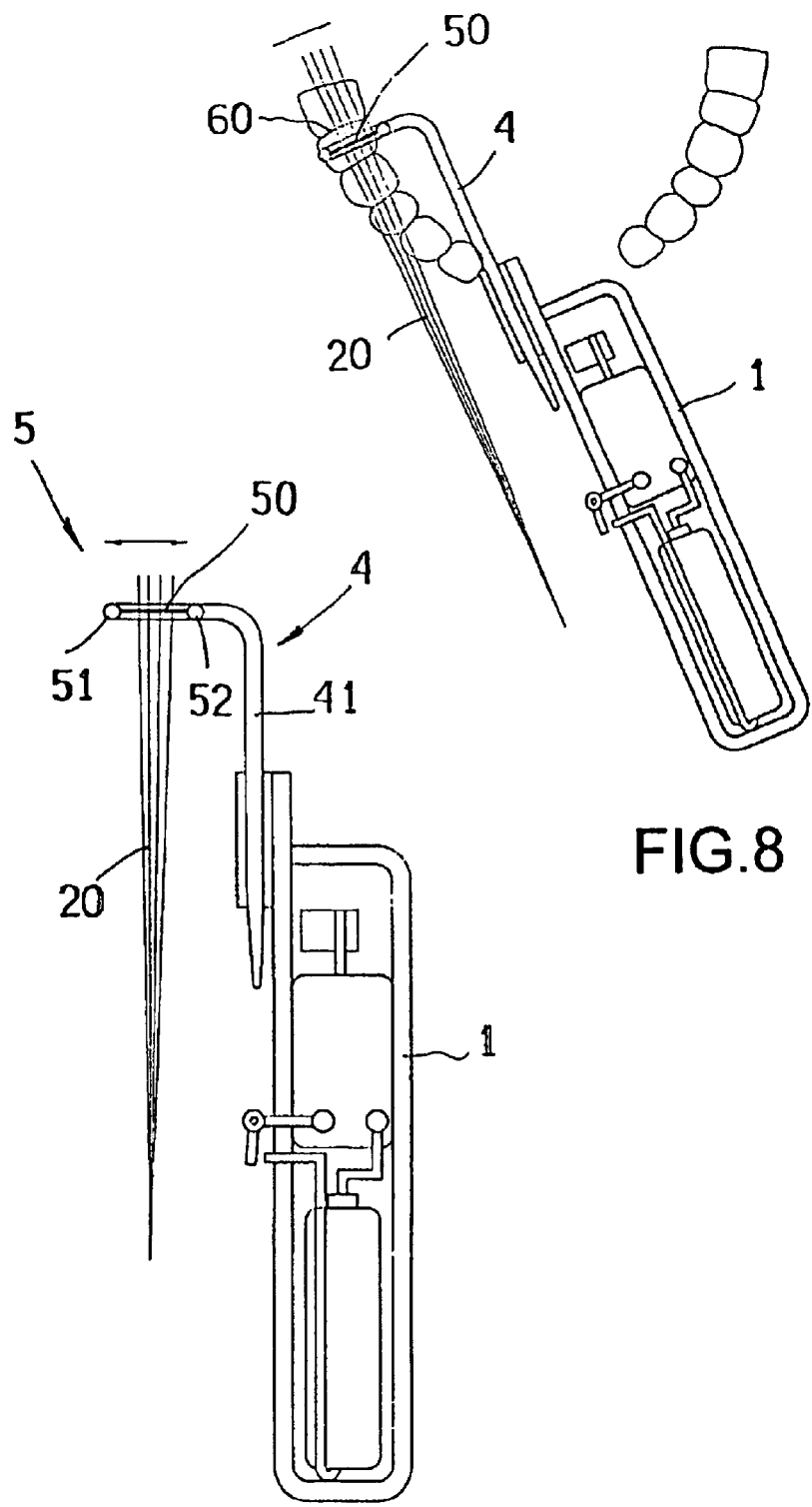
FIG. 7 is a schematic drawing of the structure of the L-shape link rod of the present invention.
FIG. 8 is a schematic drawing of the operation of the L-shape link rod of the present invention.

Referring to FIG. 7, the said link rod (4) can be designed as an L-shape to form a vertical shape between the floss bow section (5) thereof and the rod body (41); the said floss material (50) is also vertical to the holder body (1) through the form of the floss expansion ends (51, 52) disposed on the said floss bow section (5); through the working of the holder body (1), the said floss material (50) also attain a working line vertical to the vibration axis (20) for providing the operation manner as shown in FIG. 8, of conducting transverse cleansing for the tooth gaps between the jaw teeth of the oral jaw section; although the direction of the vibration is vertical, as long as the vibration exists, the auxiliary operation of ingress and egree movement will be done through operating the holder body (1) and the cleansing inside the tooth gaps (60) can also achieve the relative efficient objective.

Figures 9A, 9B:
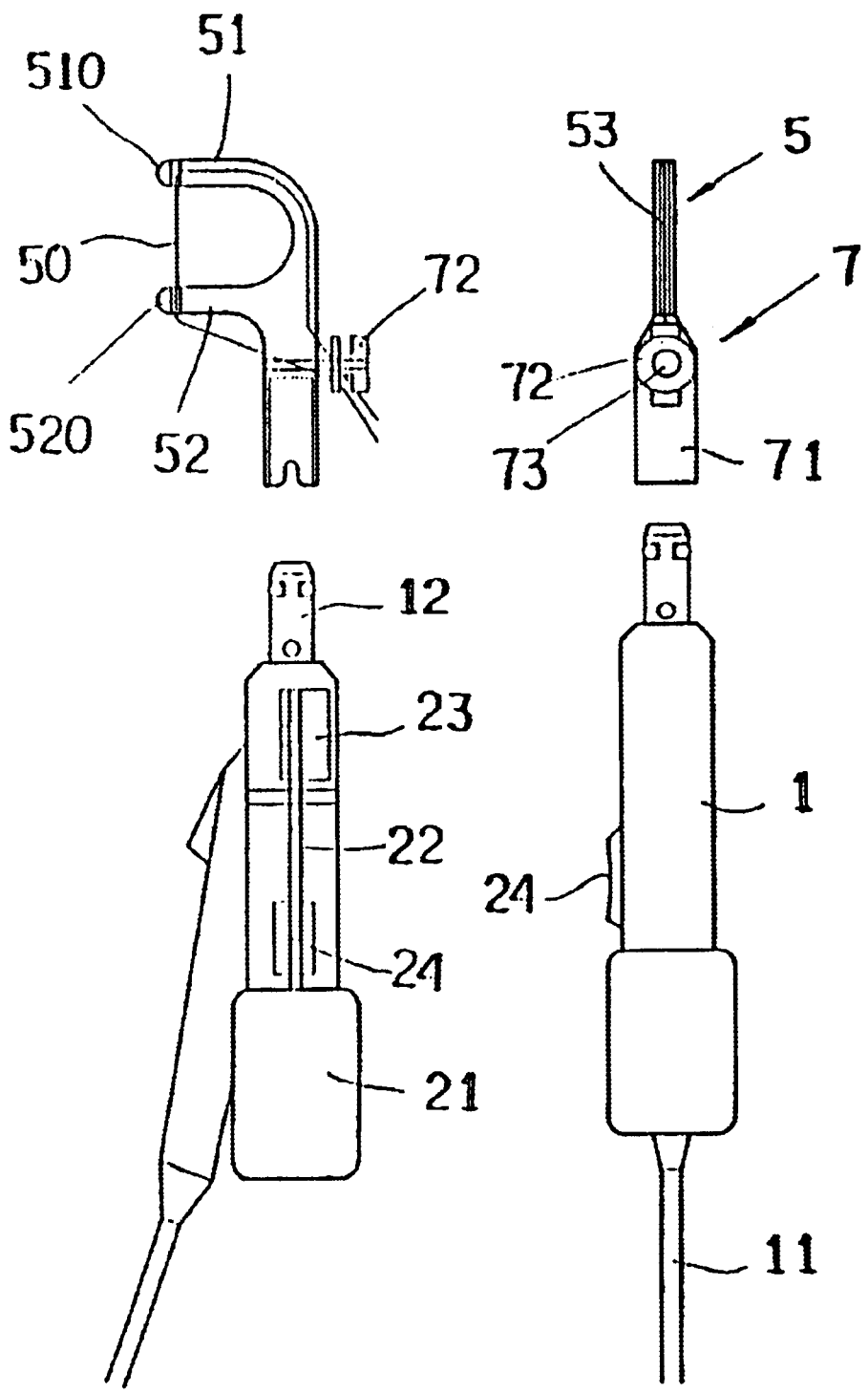
FIGS. 9A and 9B are schematic drawings of another inserted and assembled present invention.

Referring to FIGS. 9A and 9B, a motor (21) in the shape of a long shaft can be installed inside the holder body (1); through an eccentric hammer (23) disposed at the long distance on the distal end of the longer axle center (22), the said motor (21) concentrates as much as possible the working energy of the said eccentric hammer (23) at the front end of the holder body (1) (the holder body (1) obtains electricity by means of the connection of the direct current power cord (11)) for making the working force concentrate at the front distal end of the holder body (1); the distal end of the said holder body (1) can be disposed by the manner of an insert tenon (12), the said insert tenon (12) is of an axial column providing the coupling of a link member (7) mounted with an insert tube (71), the free end of the said link member (7) is also disposed with a floss bow section (5), a floss slot (53) and two floss expansion ends (51, 52) mounted with two retaining notches (510, 520) are disposed inside the said floss bow section (5); the existence of the said notches (510, 520) provides the winding manner of the floss material (50) to be secured, pressed and fixed by means of a securing screw (72) for fastening the ends of the floss material (50) at the relative positions of the screw rod (73) thereby to achieve the disposable method of the floss material (50) and further obtain the operation of the disposable floss material (50).

Figures 10A, 10B, 10C:
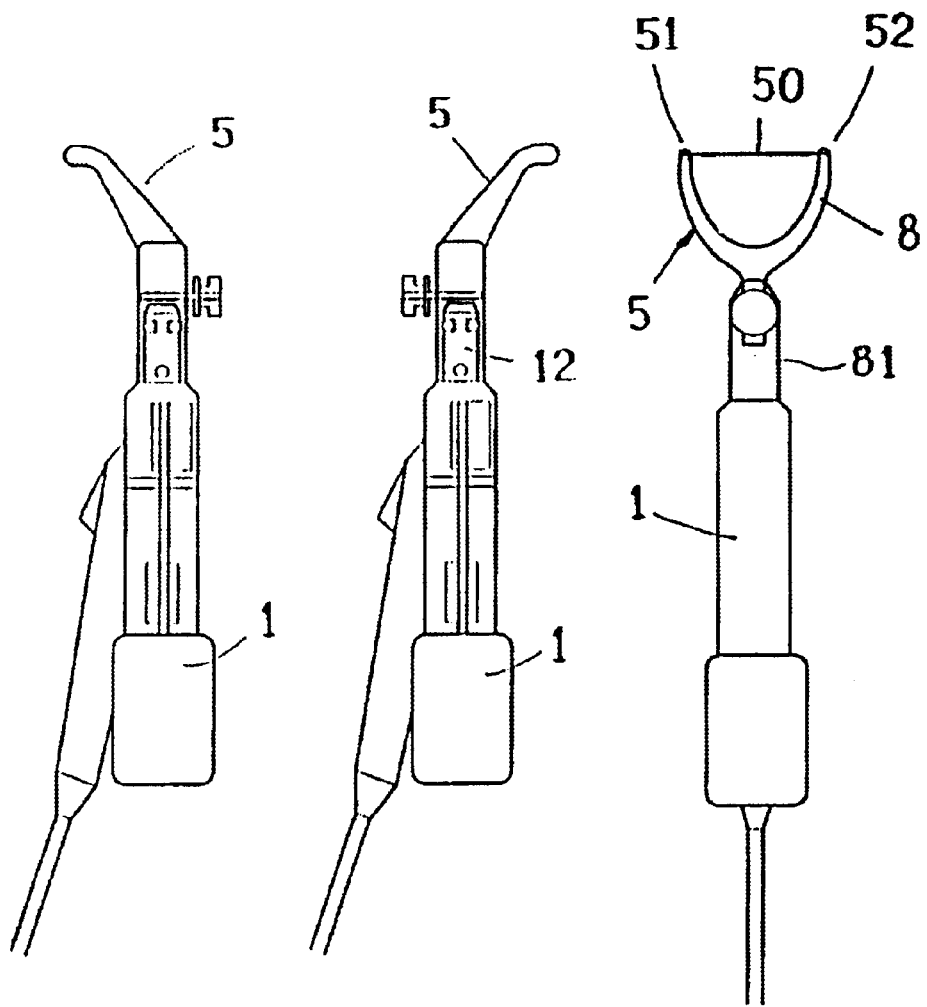
FIG. 10A, 10B and 10C are schematic drawings of another inserted and assembled present invention.

Referring to FIGS. 10A–10C, the link member (8) of the present invention can be designed as a Y-shape, the root section thereof is disposed with an insert tube (81) for inserting the insert tenon (12) mounted on the holder body (1) to achieve the assembling purpose; the lateral aspect of the said floss bow section (5) is of a bevel shape for enabling the center lines of the floss material (50) and the holder body (1) to deviate thereby to facilitate the inclining method of deep cleansing operation at the tooth root.

Figure 11:
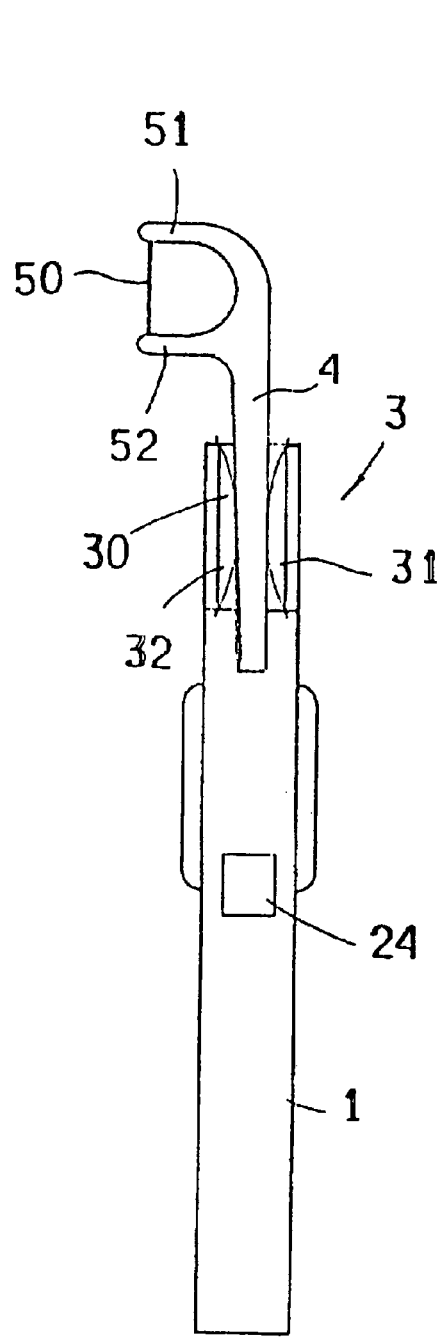
FIG. 11 is the first drawing of another exemplary embodiment of the insert section of the present invention.

Referring to FIG. 11, two elastic clamp components (31,32) can be disposed inside the insert slot (30) of the insert section (3) mounted at the distal end of the holder body (1) of the present invention, the existence of the said elastic clamp components (31, 32) provides the insertion of narrower and smaller link rod (4), the bamboo-made toothpick, etc., to obtain other kinds of auxiliary operation tool, or through the assembling operation of the toothpick stick or F-shaped toothpick, to obtain the assembly of a disposable toothpick; as shown in FIG. 1, the movable fix clamping of the link rod (4) provided in the said slot (30) enables the assembly between the floss bow section (5) and the holder body (1) to attain the displacement change and the change of the vibration amplitude of the said floss bow section (5), for example, the longer the distal end thereof is, the wider the vibration amplitude will be.

Figure 12:
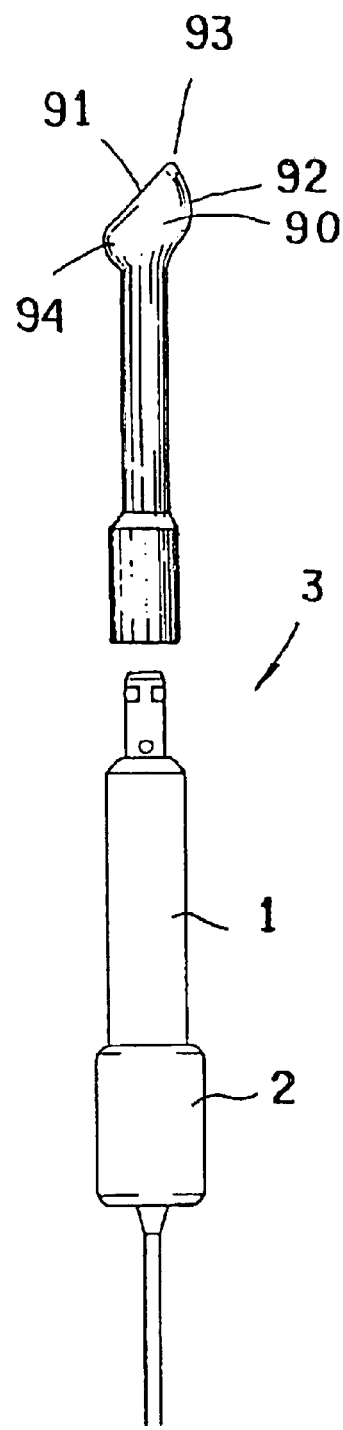
FIG. 12 is the second drawing of another exemplary embodiment of the insert section of the present invention.

Referring to FIG. 12, the insert section (3) disposed on the holder body (1) of the present invention can also provide the insertion of a massage bar (9) with one free end thereof designed as a horseshoe-shaped contact press end (90); the said massage bar (9), after being inserted, can massage the surfaces of the gums (61) or even the surfaces of the teeth (6); the said massage method can encourage the activation of the gum (61) tissues, improve the blood circulation, increase the resistance and metabolic effect thereby to enable the gums (61) to obtain renovative hygiene operation; utilizing the stimulating function of the massage bar (9) for massaging the root section of the tongue on the lower jaw in the oral cavity can stimulate the rapid generation of the saliva to moisture the mouth; the said massage bar (9) is designed as a horseshoe shape, therefore a horseshoe point (93) is formed at the distal end thereof, a horseshoe bottom (91) on one side, a horseshoe plane (92) on the other side and a horseshoe root (94) at the root section; every surface shape of the said horseshoe shapes can be used to conduct adequate contacting massage on the external surfaces of the teeth (6) or the gums (61), for example, the said horseshoe bottom (91) has larger plane, therefore it can conduct contacting massage on the larger surfaces of the gums (61), while the said horseshoe point (93) is of a pointed shape, it can conduct direct and inserting massage on the space (62) at the root section of the tooth gap (60), the smaller horseshoe plane (92) can massage the smaller area, and the horseshoe root (94) can do any corresponding massage on the shallow recessed areas of the gums (61).

The fact that the functional performance of the entire composition of the present invention can attain the massage for the teeth simultaneously during cleansing, the said insert section can use the inserting method to provide multiple disposable cleansing tools to fit the operation, the insert distance can be changed thereby to change the vibration amplitude, and the method of inserting the massage bar at the insert section can provide the multiple functional operations inside a single mechanism to obtain the renovative hygiene application for the oral cavity, qulifies the present invention for a convenient and personal owned hygiene appliance that provides the user with a whole new rapid hygienic function for the teeth and the gums.

What is claimed is:

1. A vibrating wave oral cleansing and hygiene device comprising:
   a) a holder body having:
      i) a working section connected to an interior of the holder body; and
      ii) an insert section on an end of the holder body; and
   b) a link rod having a floss bow section, the link rod and the floss bow section being integrally formed, the link rod being removably connected to the insert section of the holder body, the floss bow section having two floss expansion ends, each of the floss expansion ends having a retaining notch for securing a floss material between the two floss expansion ends and, wherein the floss bow section has a securing screw and a screw rod configured to fasten ends of the floss material, wherein the holder body further includes a motor and an eccentric hammer creating a vibration and moving the link rod in a conical path of movement.

2. The vibrating wave oral cleansing and hygiene device according to claim 1, wherein the link rod has a Y shape.

3. The vibrating wave oral cleansing and hygiene device according to claim 1, wherein the insert section has an insert slot with two elastic clamp components, the link rod has a rod body on an end opposite the floss bow section; and the rod body is removably inserted into the insert slot and frictionally engaged by the two elastic clamp components.

4. The vibrating wave oral cleansing and hygiene device according to claim 1, wherein the insert section has an insert tenon; the link rod has an insert tube on an end opposite the floss bow section, and the insert tenon is removably inserted into the insert tube.

5. The vibrating wave oral cleansing and hygiene device according to claim 1, further comprising a horseshoe shaped massage bar.

* * * * *